United States Patent
Deuel et al.

(12)

(10) Patent No.: US 6,448,381 B1
(45) Date of Patent: Sep. 10, 2002

(54) DNA ENCODING HEPARIN-BINDING GROWTH FACTOR

(75) Inventors: Thomas F. Deuel; Yue-Sheng Li, both of St. Louis, MO (US); Ned R. Siegel, Belleville, IL (US); Peter G. Milner, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 0 days.

(21) Appl. No.: 07/542,232

(22) Filed: Jun. 21, 1990

Related U.S. Application Data (63) Continuation-in-part of application No. 07/462,156, filed on Jan. 8, 1990, now abandoned.

(51) Int. Cl.[7] .......................... A61K 38/24; A61K 38/27; C07K 1/00; C07K 14/00
(52) U.S. Cl. ...................... 530/399; 530/324; 536/23.5; 536/23.51
(58) Field of Search .................................. 530/399, 324; 536/27, 23.5, 23.51

(56) References Cited

FOREIGN PATENT DOCUMENTS

EP 326075 8/1989

OTHER PUBLICATIONS

Maniahs Et Al "Mol. Cloning: A Lab Manual" (Cold Spring Harbor Laboratory) New York: 1982 pp. 353–361.*

Kris et al, Bio/Technology 3, 135–140 (1985).

Van Brunt and Klausner, Ibid. 6, 25–30 (1988).

Dijke & Iwata, Ibid. 7, 793–798 (1988).

Rauvala, EMBO J. 8, 2933–2941 (1989).

I. Kovesdi et al, Biochem. and Biophys. Res. Commun., 172, 850–854 ((1990).

J. Merenmies et al, The Journal of Biol. Chem., 265, 16721–16724 (1990).

* cited by examiner

Primary Examiner—Yvonne Eyler
(74) Attorney, Agent, or Firm—Sonnenschein Nath & Rosenthal (57) ABSTRACT

A novel heparin-binding growth factor of 18.9 kDa mol. wt. is disclosed which is purified from bovine uterus and human placenta and has a unique 25 N-terminal amino acid sequence as follows:

Gly-Lys-Lys-Glu-Lys-Pro-Glu-Lys-Lys-Val-Lys-Lys-Ser-Asp-Cys-Gly-Glu-Trp-Gln-Trp-Ser-Val-Cys-Val-Pro.

2 Claims, 3 Drawing Sheets

DNA ENCODING HEPARIN-BINDING GROWTH FACTOR

Cross-Reference to Relate Application

This is a continuation-in-part of application Ser. No. 07/462,156, filed Jan. 8, 1990.

BACKGROUND OF THE INVENTION

This invention relates to a novel peptide growth factor and, more particularly, to a heparin-binding growth factor derived from bovine uterus and human placenta.

In recent years a considerable number of growth factors derived from various animal cells have been isolated and characterized. Illustrative of these growth factors are nerve growth factor (NGF) which has been purified from several different cell sources, insulin-like growth factors (IGF-I and IGF-11), epidermal growth factor (EGF), fibroblast growth factor (FGF), platelet-derived growth factor (PDGF), endothelial cell growth factor (ECGF), somatomedins and transforming growth factors (TGF) derived from various tumors and virally transformed cells. For background information on these growth factors see, for example, the recent brief review articles by Kris et al., *Biotechnology* 3, 135–140 (1985); Dijk and Iwata, Ibid. 7, 793–798 (1989); and the comprehensive review in *Hormonal Proteins and peptides*, Ed. by Choh Hao Li, Vol. 12, "Growth Factors," Academic Press, 1984.

Although the existence of acidic and basic fibroblast growth factor (aFGF and bFGF) has been known for fifty years [Trowell, et al., J. Exp. Biol. 16, 60–70, (1939); Hoffman, Growth 4, 361–376 (1940)], only recently have they been purified and sequenced [Thomas et al., *Proc. Natl. Acad. Sci. USA* 81, 357–361 (1984); Gimenez-Gallego et al., *Science* 230, 1385–1388 (1985); Lemmon and Bradshaw, *J. Cell. Biochem.* 21, 195–208 (1983); Bohlen et al., *Proc. Natl. Acad. Sci. USA* 81, 5364–5368 (1984); and Esch et al., *Proc. Natl. Acad. Sci. USA* 82, 6507–6511 (1985)]. aFGF and bFGF have 55% sequence homology, suggesting that they arose by duplication and divergence from a common ancestral gene. Cells responding to the FGFs have between $10^3$ and $10^5$ high affinity receptors per cell [Neufeld and Gospodarowicz, *J. Biol. Chem.* 261, 5631–5637 (1986)]. The bFGF receptor has recently been purified, sequenced, and cloned [Lee et al., *Science* 245, 57–60 (1989)]. Both bFGF and aFGF compete for the same receptor and displace each other in radio-receptor assay [Neufeld, supra; Olwin and Hauschka, *Biochemistry* 25, 3487–3492 (1986)]; however, two forms of the receptor appear to have different affinities for aFGF and bFGF. Recently five additional proteins have been reported by cDNA cloning to have homology to the FGFs (hst, int-2, FGF-5, FGF-6, and KGF or FGF-7) [Dickson and Peters, *Nature* 326, 833 (1987); Yoshida et al., *Proc. Natl. Acad. Sci. USA* 84, 7305–7309 (1987); Delli Bovi et al., *Cell* 50, 729–737 (1987);.Zhan et al., *Mol. Cell. Biol.* 8, 3487–3495 (1988); Marcis et al., *Oncogene* 4, 335–340 (1989); and Finch et al., *Science* 245, 752–755 (1989)]. All five cDNA sequences encode signal peptides, therefore suggesting that these five proteins are presumably secreted, unlike aFGF or bFGF which lack signal peptides.

Brief Description of the Invention

In accordance with the resent invention a novel heparin-binding growth factor has been isolated from bovine uterus and human placenta. This novel heparin-binding growth factor, herein also designated as HBGF-8, is a 18.9 kDa polypeptide with a unique 25 N-terminal amino acid sequence as follows:

HBGF-8

Gly-Lys-Lys-Glu-Lys-Pro-Glu-Lys-Lys-Val-Lys-Lys-Ser-Asp-Cys-Gly-Glu-Trp-Gln-Trp-Ser-Val-Cys-Val-Pro.

This novel growth factor binds tightly to cation exchange resins and to Heparin-Sepharose® and is stable to acetone precipitation and labile in acid.

HBGF-B was as active as acidic fibroblast growth factor (aFGF) and slightly less active than bFGF in the mouse NIH 3T3 fibroblast mitogenic assay system with an intrinsic specific activity of 5000 dpm/ng under standard assay conditions.

In an illustrative example and based upon total activity in the acetone extracts of bovine uterus stimulating $^3$H-thymidine incorporation into DNA of serum-starved NIH 3T3 cells, a 6940 fold purification was achieved with an overall yield of HBFG-8 activity of 0.4%, using extraction of acetone powders and chromatographic separations at neutral pH. Approximately 18 µg protein was obtained from 1.2 kg wet weight of tissue. HBGF-8 was clearly separated from 17.5 kDa bovine uterus basic fibroblast growth factor (bFGF) by purification and its N-terminal amino acid sequence analysed. The unique sequence as set forth above was found.

In accordance with another aspect of the invention, the complete coding sequence of CDNA clones representing the full size bovine HBGF-8 and human HBGF-8 have been developed.

Thus, the bovine HBGF-8 cDNA sequence was isolated from bovine uterus cDNA library using the above bovine HBGF-8 N-terminal sequence clone as a probe. The cDNA sequence contains 1196 nucleotides and encodes a 18.9 kDa ($M_r$=18,902) protein of 168 amino acids, including a 32 amino acid leader sequence. The cDNA coding sequence starts at nucleotide position 170 to 673.

The human HBGF-8 cDNA sequence was isolated from human placenta cDNA library using bovine HBGF-8 cDNA fragment as a probe. The cDNA sequence contains 995 nucleotides and encodes a 18.9 kDa ($M_r$=18,942) protein of 168 amino acids, including a 32 amino acid lead sequence. The cDNA coding sequence starts at nucleotide position 252 to 755.

Comparison of the bovine and human HBGF-8 showed that HBGF-8 is highly conserved. Of 168 amino acids, 163 were identical. Differences occur at amino acid positions 3, 4 and 7 in the leader sequence and at amino acid positions 130 and 147 in the mature protein of the complete 168 amino acid sequence.

The human and bovine cDNA protein sequences and the human and bovine cDNA sequences for HBGF-8 are as follows:

Human HBGF-8 Protein

Met Gln Ala Gln Gln Tyr Gln Gln Gln Arg Arg Lys Phe Ala Ala 15

Ala Phe Leu Ala Phe Ile Phe Ile Leu Ala Ala Val Asp Thr Ala 30

Glu Ala Gly Lys Lys Glu Lys Pro Glu Lys Lys Val Lys Lys Ser 45

Asp Cys Gly Glu Trp Gln Trp Ser Val Cys Val Pro Thr Ser Gly 60

Asp Cys Gly Leu Gly Thr Arg Glu Gly Thr Arg Thr Gly Ala Glu 75

Cys Lys Gln Thr Met Lys Thr Gln Arg Cys Lys Ile Pro Cys Asn 90

Trp Lys Lys Gln Phe Gly Ala Glu Cys Lys Tyr Gln Phe Gln Ala 105

Trp Gly Glu Cys Asp Leu Asn Thr Ala Leu Lys Thr Arg Thr Gly 120

Ser Leu Lys Arg Ala Leu His Asn Ala Glu Cys Gln Lys Thr Val 135

Thr Ile Ser Lys Pro Cys Gly Lys Leu Thr Lys Pro Lys Pro Gln 150

Ala Glu Ser Lys Lys Lys Lys Glu Gly Lys Lys Gln Glu Lys 165

Met Leu Asp 168

Bovine HBGF-8 Protein

Met Gln Thr Pro Gln Tyr Leu Gln Gln Arg Arg Lys Phe Ala Ala 15

Ala Phe Leu Ala Phe Ile Phe Ile Leu Ala Ala Val Asp Thr Ala 30

Glu Ala Gly Lys Lys Glu Lys Pro Glu Lys Lys Val Lys Lys Ser 45

Asp Cys Gly Glu Trp Gln Trp Ser Val Cys Val Pro Thr Ser Gly 60

Asp Cys Gly Leu Gly Thr Arg Glu Gly Thr Arg Thr Gly Ala Glu 75

Cys Lys Gln Thr Met Lys Thr Gln Arg Cys Lys Ile Pro Cys Asn 90

Trp Lys Lys Gln Phe Gly Ala Glu Cys Lys Tyr Gln Phe Gln Ala 105

Trp Gly Glu Cys Asp Leu Asn Thr Ala Leu Lys Thr Arg Thr Gly 120

Ser Leu Lys Arg Ala Leu His Asn Ala Asp Cys Gln Lys Thr Val 135

Thr Ile Ser Lys Pro Cys Gly Lys Leu Thr Lys Ser Lys Pro Gln 150

Ala Glu Ser Lys Lys Lys Lys Glu Gly Lys Lys Gln Glu Lys 165

Met Leu Asp 168

| HUMAN HBGF-8 cDNA | | | | |
|---|---|---|---|---|
| GTCAAAGGCA | GGATCAGGTT | CCCCGCCTTC | CAGTCCAAAA | ATCCCGCCAA | 50 |
| GAGAGCCCCA | GAGCAGAGGA | AAATCCAAAG | TGGAGAGAGG | GGAAGAAAGA | 100 |
| GACCAGTGAG | TCATCCGTCC | AGAAGGCGGG | GAGAGCAGCA | GCGGCCCAAG | 150 |
| CAGGAGCTGC | AGCGAGCCGG | GTACCTGGAC | TCAGCGGTAd | CAACCTCGCC | 200 |
| CCTTGCAACA | AAGGCAGACT | GAGCGCCAGA | GAGGACGTTT | CCAACTCAAA | 250 |
| AATGCAGGCT | CAACAGTACC | AGCAGCAGCG | TCGAAAATTT | GCAGCTGCCT | 300 |
| TCTTGGCATT | CATTTTCATA | CTGGCAGCTG | TGGATACTGC | TGAAGCAGGG | 350 |
| AAGAAAGAGA | AACCAGAAAA | AAAAGTGAAG | AAGTCTGACT | GTGGAGAATG | 400 |
| GCAGTGGAGT | GTGTGTGTGC | CCACCAGTGG | AGACTGTGGG | CTGGGCACAC | 450 |
| GGGAGGGCAC | TCGGACTGGA | GCTGAGTCCA | AGCAAACCAT | GAAGACCCAG | 500 |
| AGATGTAAGA | TCCCCTGCAA | CTGGAAGAAG | CAATTTGGCG | CGGAGTGCAA | 550 |
| ATACCAGTTC | CAGGCCTGGG | GAGAATGTGA | CCTGAACACA | GCCCTGAAGA | 600 |
| CCAGAACTGG | AAGTCTGAAG | CGAGCCCTGC | ACAATGCCGA | ATGCCAGAAG | 650 |
| ACTGTCACCA | CTCCCAAGCC | CTGTGGCAAA | CTGACCAAGC | CCAAACCTCA | 700 |
| AGCAGAATCT | AAGAAGAAGA | AAAAGGAAGG | CAAGAAACAG | GAGAAGATGC | 750 |
| TGGATTAAAA | GATGTCACCT | GTGGAACATA | AAAAGGACAT | CAGCAAACAG | 800 |
| GATCAGTTAA | CTATTGCATT | TATATGTACC | GTAGGCTTTG | TATTCAAAAA | 850 |
| TTATCTATAG | CTAAGTACAC | AATAAGCAAA | AACAAAAAGA | AAAAAAAAA | 900 |
| AAAAAAAAAA | AAAAAAAAA | AAAAAAAAA | AAAAAAAAA | AAAAAAAAA | 950 |
| AAAAAAAAA A | | | | | 961 |

| Bovine HBGF-8 cDNA | | | | |
|---|---|---|---|---|
| GAGTGGAGAG | AGTAGAAGAA | AGAGAGCAGG | GAGTCACCGG | GCGTGCGGGG | 50 |
| GCGGAGAGCA | GCGGCCGCCG | CGAGCACCAG | CGACTTGGGT | ACCTGGACTC | 100 |

-continued

Bovine HBGF-8 cDNA

```
AGGGCAGAAA AACCTCTCCC GGATCAACAA AGGCAGCCTG AGCGCGCACC  150

GCTCTTTTGC GACTCCAAAA TGCAGACTCC ACAGTACCTG CAGCAACGTC  200

GAAAATTTGC AGCTGCCTTT TTGGCATTTA TTTTCATCTT GGCAGCTGTG  250

GACACCGCTG AAGCAGGAAA GAAAGAGAAA CCAGAAAAGA AGGTGAAGAA  300

GTCTGACTGT GGAdAATGGC AGTGGAGTGT GTGTGTACCA ACCAGTGGGG  350

ACTGTGGGCT GGGCACCCGC GAGGGCACCC GTACCGGAGC TGAGTGTAAA  400

CAAACCATGA AGACCCAGAG ATGTAAGATC CCCTGCAACT GGAAAAAGCA  450

ATTTGGAGCG GAGTGCAAAT ACCAGTTCCA GGCCTGGGGA GAATGTGATC  500

TGAACACGGC TCTGAAGACC CGAACTGGGA GCCTGAAGCG AGCCCTCCAC  550

AACGCCGACT GCCAGAAGAC AGTCACCATC TCCAAGCCCT GTGGCAAGCT  600

GACCAAGTCC AAACCTCAAG CAGAATCTAA GAAGAAGAAA AAGGAAGGCA  650

AGAAACAGGA GAAGATGCTG GACTAAAAGC CACCACCTTC CGTGGACCAT  700

GAAAAGGACA TCAGCAAACA CGATCAGTTA ACTATTGCAT TTATATCTAC  750

CGTAGGCTTT TTATTCAAAA ATTATCTATA GCTTAAGTAC ACAATAGGCA  800

GAAACAAAAT GAAAAGAAAA ATTTTGTAGT AGCATTTTTT TTAAATGTAT  850

CAATATACCA TAGTACCACT AGGGACTTAT AATAGAGGAC TGTAATCCTA  900

TTTAGAATGT TGACTTATAG TACATGTTAA GTGATAGAAA ACTGAGGTAA  950

GTTTTTTGAA GTTATGTGAT ATTTTACATT ACATTTTTTT TTACATTTTT 1000

TTCTTTTGGC AGCAATTTAA ATGTTATGAC TATGTAAACT ACTTCTCTTG 1050

TTAGGTAATT TTTTTCACCT AGACTTTATT TCCCAATTGA GAAAAATATC 1100

TACTAAACAA AGCAGCAATA AAATATGATC ATCCTATCTG AGGAAAATAT 1150

CTCTTTTTCT GCCAGTGGAT TTTTAAAAAA TTGTAGTCAA CAAAAT      1196
```

In the bovine HBGF-8 protein sequence, the following amino acid replacements of the human sequence are found:
Ala-3→Thr; Gln-4→Pro; Gln-7→Leu; Glu-130→Asp; and Pro-147→Ser.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in connection with the accompanying drawings in which briefly:

BRIEF DESCRIPTION OF THE FIGURES

FIG. 1 is a graphical representation which shows Chromatographic separation of Bovine Uterus Mitogenic Activity. The mitogenic activity that bound to Heparin-Sepharose between 900 mM and 2000 mM NaCl was concentrated from 1160 ml to 12 ml using a MonoS HR 10/10 column, elution of this column using 2000 mM NaCl, and reapplication following dilution to 500 mM NaCl to the MonoS HR 5/5 column shown above. The $A_{280}$ absorption profile elution of protein is shown by the shaded area. The results of the solid phase ELISA to detect bovine bFGF immunoreactivity are shown by the open triangles. In addition, the mitogenic activity in the mouse NIH 3T3 assay system is shown by the open squares. The NaCl gradient that was applied from 500 mM to 2000 mM salt is shown by the dashed line and individual fractions of 1 ml were collected. The bFGF immunoreacitivty is expressed as µg/ml of bFGF. The region of the column shown by the continuous line and labeled region A was pooled, dialyzed, concentrated and applied to the microbore cation exchange column.

FIG. 3 shows the SDS-PAGE of the pure bovine uterus bFGF and HBGF-8. Lane 1 shows the appearance after SDS-PAGE in 15% gels of the pure 17.5 kD bovine uterus bFGF following reverse phase C4 chromatographic purification. This material was used for N-terminal sequencing. Lane 2 shows the appearance of the 17 kD novel HBGF-8 in the same gel system. This tube was used for determining novel N-terminal amino acid sequence shown above. The molecular weight markers used were BRL low molecular weight range markers.

In order to illustrate specific preferred embodiments of the invention in greater detail, the following exemplary laboratory preparative work was carried out. It will be appreciated, however, that the invention is not limited to these specific examples or the details described therein.

EXAMPLE 1

METHODS

Mitogenic Assays. The mitogenic activity of samples was assayed in triplicate by measuring the incorporation of [methyl-$^3$H] thymidine into acid-insoluble DNA of confluent, serum-starved NIH 3T3 cells. Unstimulated cells were used as background and values subtracted as background, which averaged 1500 dpm.

Immunological Methods. Rabbit anti-bFGF polyclonal antisera were obtained from Dr. Judith Abraham (California Biotechnology, Inc.). The solid phase immunosorbant assay used to screen column fractions was carried out by conventional procedure as previously described by Yeh et al., *Proc. Natl. Acad. Sci. USA* 84, 2317–2321 (1987).

Extraction of Growth Factor Activity from Acetone Powders. The acetone powders were prepared by conventional procedure as previously described by Porter et al., *J. Biol. Chem.* 263, 8989–8995 (1988), extracted with 40 ml/g of 0.9 M NaCl, 20 mM Tris-HCl (pH 8.0), 5 mM [ethylenebis (oxyethylenenitrilo)] tetra-acetic acid (EGTA), 0.15 mg/ml phenylmethylsulphonyl fluoride. 10 mM benzamidine, 0.1 mg/ml soybean trypsin inhibitor, and 1 µg/ml aprotinin for 2 h at 4° C. with agitation, and centrifuged at 10,000×g for 30 min.

Heparin-Sepharose Chromatography. 6.9 liters of the soluble extract (34.5 g protein) was diluted to 20.7 liters in 900 mM NaCl, 20 mM Hepes, pH 7.0, loaded onto a 5×12.5 cm Heparin-Sepharose (Pharmacia) column at 4° C. at a flow rate of 5 ml/min, washed in 10 column volumes of the starting buffer, 20 mM Hepes, pH 7.0, 900 mM NaCl, and eluted with 1160 ml of 20 mM Hepes, pH 7.0, 2 M NaCl, at a flow rate of 1 ml/min. The eluted fraction (2 M NaCl) was dialyzed against 20 mM MES, pH 6.0. Hepes=N-[2-Hydroxyethyl]piperazine-N'-[2-ethanesulfonic acid]. MES= 2[N-Morpholino]ethanesulfonic acid.

MonoS Chromatographic Separation of Mitogenic Activity. The active fraction (20 mM MES, pH 6.0) was loaded onto a MonoS HR 10/10 column (Pharmacia, FPLC) at 2.5 ml/min, washed with 10 column volumes of starting buffer, eluted with 12 ml (1.5 column volumes) of 20 mM MES, pH 6.0, 2 M NaCl, at a flow rate of 2.5 ml/min., diluted 1:4 with 20 mM MeS, pH 6.0 (final volume, 48 ml, 20 mM MES, pH 6.0, 500 mM NaCl), and loaded at 0.5 ml/min onto a MonoS HR 5/5 column (Pharmacia). Following loading, the column was washed with 10 column volumes of loading buffer and eluted with a 33 ml gradient from 500 mM NaCl to 2 M NaCl in 20 mM MES (pH 6.0). The column was further eluted with 2 M NaCl (10 ml) and the 1 ml fractions assayed in the NIH 3T3 mitogenic assay system. Each fraction also was assayed for bFGF immunoreactive proteins using a solid phase ELISA.

Microbore Cation Exchange Chromatography. The fractions (region A, FIG. 1, Mono HR 5/5 column) were pooled, dialyzed against 2 mM Hepes, pH 7.0, concentrated (1 ml), and loaded on a 2.1×220 mm aquapore CX-300 weak cation exchange column (Brownlee Labs) at a flow rate of 200 µl/min (Applied Biosystems, Inc., Model 130A Microbore HPLC system). The column was eluted with a 0–2 M NaCl gradient (15 ml, 20 mM Hepes, pH 7.0) at a flow rate of 200 pl/min and fractions assayed in the NIH 3T3 assay system for mitogenic activity.

Reverse Phase Chromatographic Purification of bFGF. The fractions containing immunoreactive bFGF were loaded on a 2.1×220 nm Aquapore BU-300 C4 reverse phase column (Brownlee Labs, Applied Biosystems HPLC System), the column equilibrated with 100% water, 0.1% TFA, and eluted with a 15 ml gradient from 0–100% acetonitrile/0.1% TFA at a flow rate of 200 µl/min. TFA =trifluoroacetic acid.

N-Terminal Amino Acid Sequencing. Fractions were analyzed by repetitive sequence analysis on a gas phase sequencer (Model 470A, Applied Biosystems, Inc.) essentially as described by Hunkapiller et al., *Meth. Enzymol.* 91, 399–412 (1983). The respective PTH-aa derivatives were identified using an Applied Biosystems Model 120A PTH analyzer. The initial yields on sequencing both proteins were 185 and 2475 pmoles for the bFGF and HBGF-8, respectively. Sequence purity averaged greater than 95% for both sequences.

RESULTS

Purification of Heparin-Binding Growth Factor-B (HBGF-8). The purification scheme for bovine uterine HBGF-8 is shown in Table 1. 1.2 kg of frozen bovine uterus yielded 18 µg of nearly pure HBGF-8 with an intrinsic specific activity in an NIH 3T3 cell mitogen assay of 5000 dpm/ng. Comparable values for aFGF and bFGF were 4090 and 9000 dpm/ng, respectively. Ten µg bFGF per 1.2 kg wet weight of bovine uterus was also obtained (see alternative method, above). An overall recovery of 0.4% of HBGF-B activity with a 6944 fold purification was obtained; because uterus contains other growth factors active in mitogenic assays using NIH 3T3 cells as targets, the recovery is grossly underestimated due to the initial inclusion of all growth factors active against NIH 3T3 cells in assay of crude extracts of bovine uterus.

Figure 1:
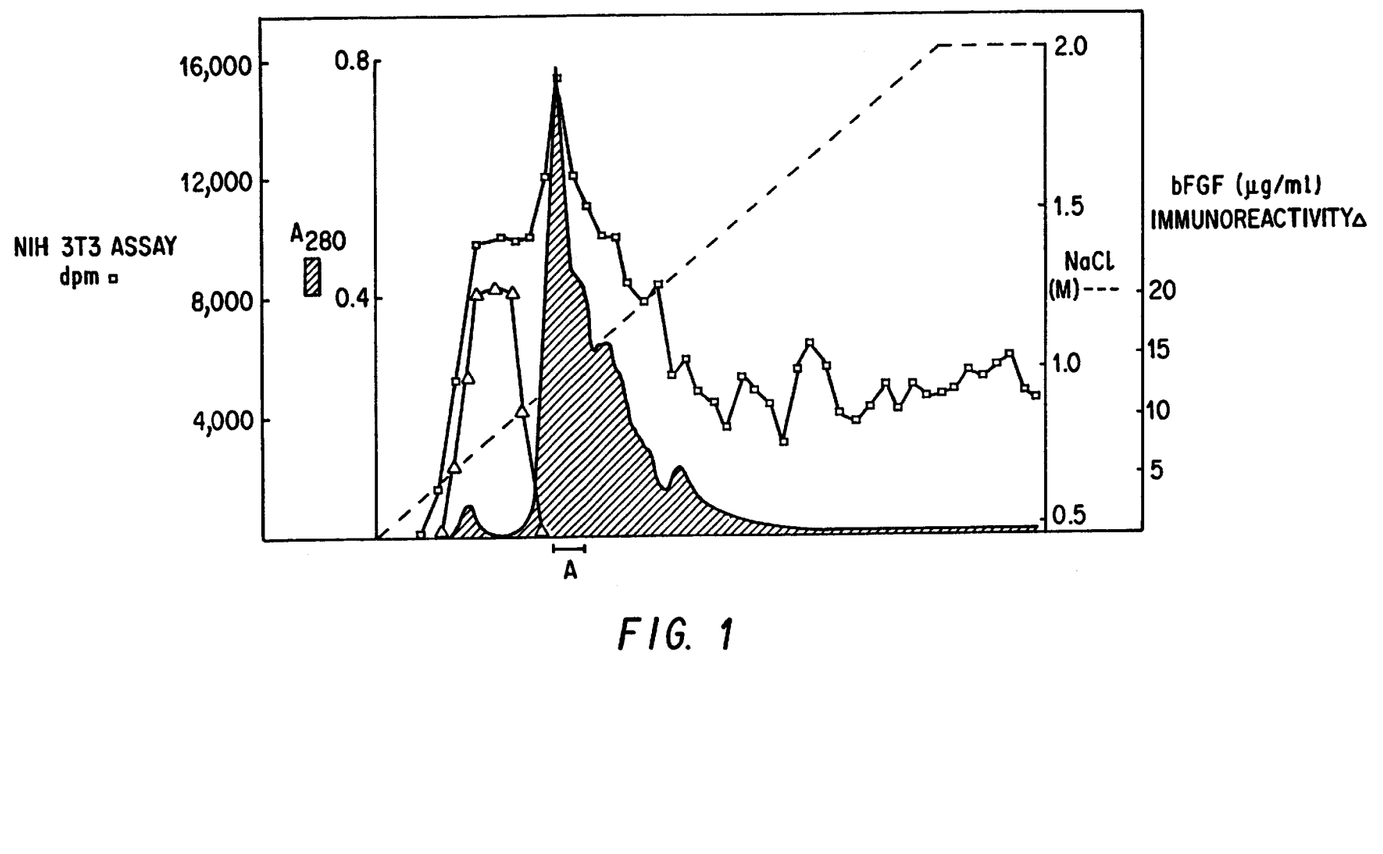

The MonoS HR 5/5 column used to further separate the mitogenic proteins binding to Heparin-Sepharose is shown in FIG. 1. bFGF immunoreactivity and mitogenic activity are shown. bFGF eluted at 0.8 M NaCl; it is both immunoreactive and a potent mitogen in the NIH 3T3 assay system. Importantly, significant activity bound to MonoS more tightly than bFGF; this data first suggested the presence of a novel growth factor.

Figure 2:
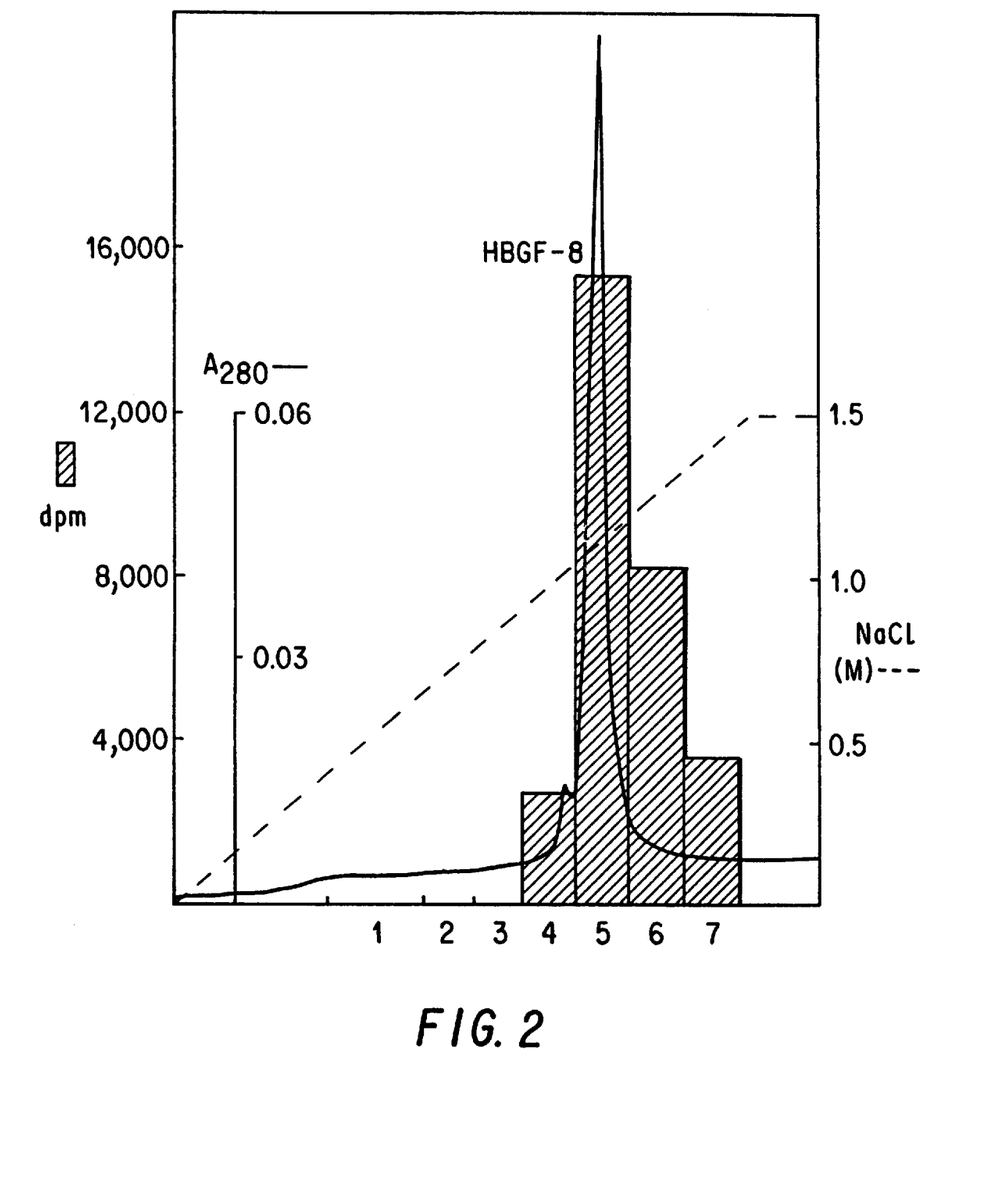
FIG. 2 is a graphical representation which shows cation exchange chromatographic separation of mitogenic proteins from bovine uterus. Region A (FIG. 1) was applied to a 2.1×220 nm Aquapore CX-300 cation exchanger and a 0–2 M NaCl gradient applied. The gradient is shown by the dashed line and the elution pattern of the proteins or $A_{280}$ by the continuous line; the histogram shows the mitogenic activity of the fractions in the NIH 3T3 assay system. The HBGF-8 peak of mitogenic activity can be seen to elute at molarity of 1–1.2 M salt.
Figure 3:
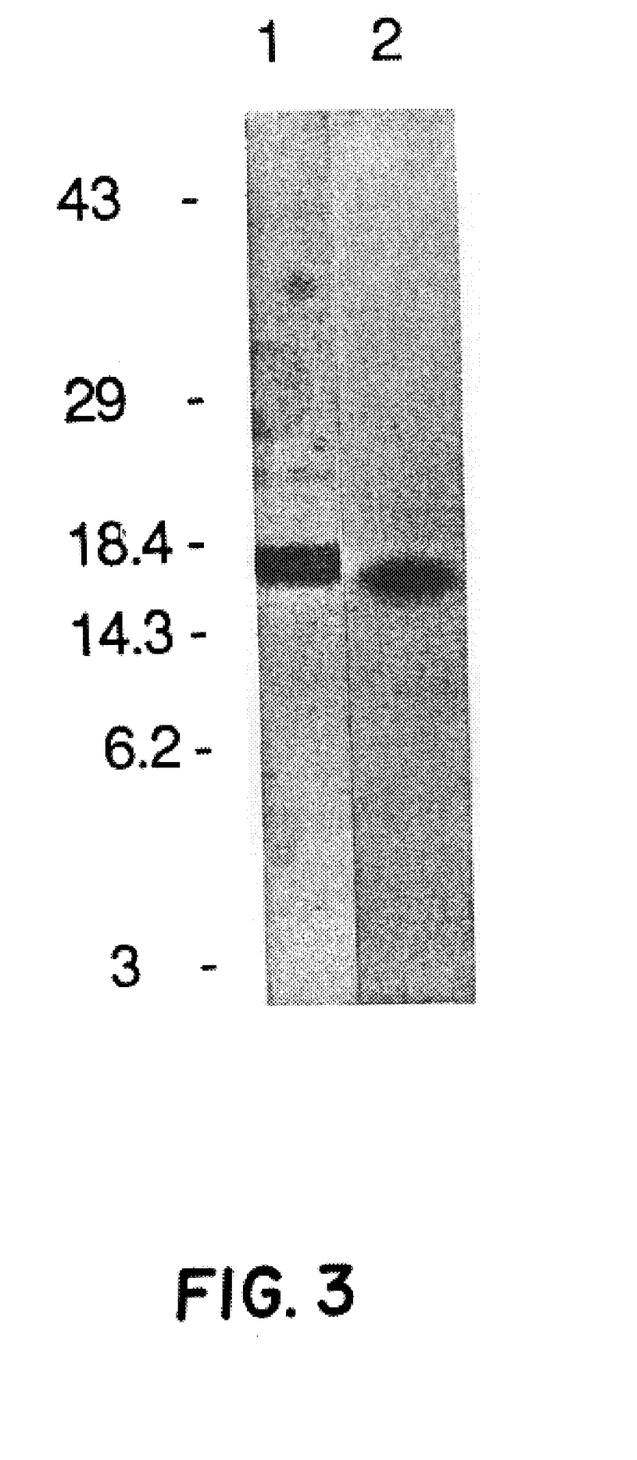

The fractions indicated by the solid bar, region A, were pooled, dialyzed, concentrated and loaded onto the microbore CX-300 cation exchange column for elution with a 0.0–2.0 M NaCl gradient. The mitogenic activity identified (FIG. 2) corresponded to a 17 kD protein when analyzed in SDS-PAGE gels under reducing conditions. The appearance of the 17.5 kD bFGF and the novel 17 kD HBGF-8 by SDS-PAGE are shown in FIG. 3.

N-Terminal Amino Acid Sequencing. The separation of bFGF from HBGF-8 was pursued by N-terminal amino acid sequencing. The bFGF was further purified by C4 reverse phase chromatography to yield a single silver-stainable band at 17 kD on SDS-PAGE. N-terminal amino acid sequencing revealed N-terminal sequences for the bovine uterus bFGF proteins as shown in Table II. The N-terminal sequence confirmed that there is an N-terminal 2 amino acid extension beyond the first methionine sequenced (at position 3) which, during initial purifications of bFGF, was thought to be the site of initiation [Abraham et al., *EMBO J*. 5, 2523–2528 (1986)]. This N-terminal sequence obtained corresponded precisely with the N-terminal amino acid sequence for human placental bFGF [Sommer et al., *Biochem. Biophys. Res. Commun*. 144, 543–550 (1987)]. Alanine-2 in the bovine uterus bFGF sequence is substituted for threonine-2 in the human bFGF sequence.

A novel 25 amino acid N-terminal sequence was then obtained for HBGF-8, as shown in Table II, confirming the separation of two high affinity heparin-binding growth factors from bovine uterus. The sequence is extremely rich in lysines (7 of the first 12 amino acids). A search of both NBRF and GENBANK data bases failed to reveal sequence homology to any known protein or gene product. Thus, although bFGF and HBGF-8 elute nearly together from various columns and migrate nearly identically by SDS-PAGE, each may be separated from the other and each have different N-terminal amino acid sequence.

HBGF-8 is both a potent mitogen and abundant in uterus. It has an intrinsic specific activity in the NIH 3T3 assay system which is roughly equal within methods of assay to aFGF and bFGF. aFGF could not be detected among the growth factors in bovine uterus which bound to Heparin-Sepharose at 900 mM NaCl. The 25 amino acid N-terminal sequence of HBGF-8 has not been identified in any of the seven members of the FGF family; aFGF [Gimenez-Gallego, supra.], bFGF [Sommer et al., supra.], int-2 [Dickson and Peters, supra.], hst [Yoshida et al., supra.], FGF-5 [Zhan et al., supra.], FGF-5 [Marcis et al., supra.], FGF-6 [Finch et al., supra.].

HBGF-8 was purified with aqueous columns with pH values between 6.0 and 7.0 About 18 μg/kg wet weight of tissue of HBGF-8 and ~10 μg/kg wet weight tissue of bFGF were recovered. However, it is likely that there may be more HBGF-8 in uterus than 18 μg/kg if all the activity which binds more tightly than bFGF in FIG. 1 is due to HBGF-8. Recently, aFGF has been shown to be more abundant than formerly thought with a tissue level of 500 μg/kg in heart [Sasaki et al., *J. Biol. Chem*. 264, 17606–17612 (1989)].

TABLE I

HBGF-8 purification scheme

|  | Total protein (mg) | Volume (ml) | Mitogenic activity* (dpm × 10⁶) | Specific activity§ | Degree purification | Yield (%) |
| --- | --- | --- | --- | --- | --- | --- |
| Solubilize acetone extract | †34,500 | 6,900 | 25,000 | 0.72 | 0 | 100 |
| 900–2000 mM elution off heparin-sepharose | 23 | 1,160 | 2,900 | 126 | 175 | 11.6 |
| 0–2000 mM elution off MonoS HR 10/10 | 3 | 12 | 433 | 144 | 200 | 1.7 |
| 500-1000 mM elution off Monos HR 5/5 | 0.2 | 10 | 250 | 1250 | 1736 | 1.0 |
| 0–2000 mM elution off CX-300 cation exchange column | 0.018 | 0.6 | 90 | 5000 | 6944 | 0.4 |

*NIH 3T3 cell assay
§Units of specific activity are dpm × 10⁶/mg protein
†1.2 Kg frozen bovine uterus yields 207 g acetone insoluble powder, which on dissolving in 900 M NaCl, 50 mM Hepes pH 7.0, produced solution containing 34.5 g of protein.

TABLE II

Bovine uterus bFGF and HBGF-8 N-terminal sequence bFGF
80% GLY-ALA-MET-ALA-ALA-GLY-SER-ILE-THR-THR-LEU-PRO-ALA-LEU-
10%         MET-ALA-ALA-GLY-SER-ILE-THR-THR-LEU-PRO-ALA-LEU-
10%                                                 PRO-ALA-LEU- HBGF-8
95% GLY-LYS-LYS-GLU-LYS-PRO-GLU-LYS-VAL-LYS-LYS-SER-ASP-
    CYS-GLY-GLU-TRP-GLN-TRP-SER-VAL-CYS-VAL-PRO.

EXAMPLE 2

Male term placenta was flash-frozen as 1 cm dice in liquid nitrogen and stored at −70° C. Total cellular and poly(A)+ RNA was prepared from placenta according to the conventional procedure of Chirgwin et al., *Biochemistry* 18, 5294–5299(1979), as modified by Sadler et al., *Proc. Natl. Acad. Sci. USA* 82, 6394–6398 (1985). cDNA was synthesized and constructed in λgt11 arms and packaged by the published method of Ye et al., *J. Biol. Chem*. 262, 3710–3725 (1987). Approximately 1×10⁶ clones from the human placenta cDNA library were screened with a bovine cDNA probe. The screening procedure was as follows: the recombinant phages were replicated onto nitrocellulose filters and hybridized overnight at 42° C. with random primer-labeled bovine cDNA probe using [α-$^{32}$P]dCTP (3,000 Ci/mmol, NEN), in 50% formamide, 50 mM sodium phosphate (pH 7.0), 5× Denhardt's Solution, 0.1 mg/ml purified tRNA and 5× standard saline citrate (SSC) (1×SSC is 150 mM sodium chloride, 15 mM sodium citrate). Filters were washed with 0.2×SSC and 0.1% SDS at 68° C. and exposed to Kodak X-Omat AR film. After tertiary screening, a positive cDNA clone was subcloned into Bluescript (Stratagene). The nucleotide sequences were obtained by the well-known dideoxy chain termination method of Sanger et al., Proc. Natl. Acad. Sci. USA 74, 5463 (1977), with Sequenase version 2.0 (U.S. Biochemicals). The sequences were obtained by sequencing both strands of DNA twice with different primers.

The human HBGF-8 cDNA sequence revealed an open reading frame which encodes a putative 168 amino acid polypeptide with a calculated molecular weight of 18,942 daltons. A 25 amino acid sequence, which was identical to the experimentally determined N-terminal sequence of purified bovine HBGF-8, began 32 amino acids downstream of the proposed initiation codon. It also shows a hydrophobic N-terminal region of 32 amino acid residues which is believed to be a leader sequence. Comparison of predicted amino acid sequences of human and bovine HBGF-8 showed that HBGF-8 is highly converved. Of 168 amino acid residues, 163 are identical.

Standard biochemical nomenclature is used herein in which the nucleotide bases are designated as adenine (A); thymine (T); guanine (G); and cytosine (C). Corresponding nucleotides are, for example, deoxyadenosine-5'-triphosphate (dATP). As is conventional for convenience in the structural representation of a DNA nucleotide sequence, only one strand is usually shown in which A on one strand connotes T on its complement and G connotes C.

Amino acids are shown herein by standard three letter abbreviations as follows:

| Abbreviated Designation | Amino Acid |
| --- | --- |
| Ala | Alanine |
| Cys | Cysteine |
| Asp | Aspartic acid |
| Glu | Glutamic acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |

-continued

| Abbreviated Designation | Amino Acid |
| --- | --- |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Various other examples will be apparent to the person skilled in the art after reading the disclosure herein without departing from the spirit and scope of the invention and it is intended that all such examples be included within the scope of the appended claims.

What is claimed is:

1. A purified and isolated DNA sequence consisting of a sequence encoding bovine heparin binding growth factor of 168 amino acids having the following amino acid sequence:

Met Gln Thr Pro Gln Tyr Leu Gln Gln Arg Arg Lys Phe Ala Ala 15

Ala Phe Leu Ala Phe Ile Phe Ile Leu Ala Ala Val Asp Thr Ala 30

Glu Ala Gly Lys Lys Glu Lys Pro Glu Lys Lys Val Lys Lys Ser 45

Asp Cys Gly Glu Trp Gln Trp Ser Val Cys Val Pro Thr Ser Gly 60

Asp Cys Gly Leu Gly Thr Arg Glu Gly Thr Arg Thr Gly Ala Glu 75

Cys Lys Gln Thr Met Lys Thr Gln Arg Cys Lys Ile Pro Cys Asn 90

Trp Lys Lys Gln Phe Gly Ala Glu Cys Lys Tyr Gln Phe Gln Ala 105

Trp Gly Glu Cys Asp Leu Asn Thr Ala Leu Lys Thr Arg Thr Gly 120

Ser Leu Lys Arg Ala Leu His Asn Ala Asp Cys Gln Lys Thr Val 135

Thr Ile Ser Lys Pro Cys Gly Lys Leu Thr Lys Ser Lys Pro Gln 150

Ala Glu Ser Lys Lys Lys Lys Glu Gly Lys Lys Gln Glu Lys 165

Met Leu Asp 168.

2. The cDNA of bovine heparin-binding growth factor having the following nucleotide sequence:

```
GAGTGGAGAG AGTAGAAGAA AGAGAGCAGG GAGTCACCGG GCGTGCGGGG    50

GCGGAGAGCA GCGGCCGCCG CGAGCACCAG CGACTTGGGT ACCTGGACTC   100

AGGGCAGAAA AACCTCTCCC GGATCAACAA AGGCAGCCTG AGCGCGCACC   150

GCTCTTTTGC GACTCCAAAA TGCAGACTCC ACAGTACCTG CAGCAACGTC   200

GAAAATTTGC AGCTGCCTTT TTGGCATTTA TTTTCATCTT GGCAGCTGTG   250

GACACCGCTG AAGCAGGAAA GAAAGAGAAA CCAGAAAAGA AGGTGAAGAA   300

GTCTGACTGT GGAGAATGGC AGTGGAGTGT GTGTGTACCA ACCAGTGGGG   350

ACTGTGGGCT GGGCACCCGC GAGGGCACCC GTACCGGAGC TGAGTGTAAA   400

CAAACCATGA AGACCCAGAG ATGTAAGATC CCCTGCAACT GGAAAAAGCA   450
```

-continued

```
ATTTGGAGCG GAGTGCAAAT ACCAGTTCCA GGCCTGGGGA GAATGTGATC    500

TGAACACGGC TCTGAAGACC CGAACTGGGA GCCTGAAGCG AGCCCTCCAC    550

AACGCCGACT GCCAGAAGAC AGTCACCATC TCCAAGCCCT GTGGCAAGCT    600

GACCAAGTCC AAACCTCAAG CAGAATCTAA GAAGAAGAAA AAGGAAGGCA    650

AGAAACAGGA GAAGATGCTG GACTAAAAGC CACCACCTTC CGTGGACCAT    700

GAAAAGGACA TCAGCAAACA CGATCAGTTA ACTATTGCAT TTATATCTAC    750

CGTAGGCTTT TTATTCAAAA ATTATCTATA GCTTAAGTAC ACAATAGGCA    800

GAAACAAAAT GAAAAGAAAA ATTTTGTAGT AGCATTTTTT TTAAATGTAT    850

CAATATACCA TAGTACCACT AGGGACTTAT AATAGAGGAC TGTAATCCTA    900

TTTAGAATGT TGACTTATAG TACATGTTAA GTGATAGAAA ACTGAGGTAA    950

GTTTTTTGAA GTTATGTGAT ATTTTACATT ACATTTTTTT TTACATTTTT   1000

TTCTTTTGGC AGCAATTTAA ATGTTATGAC TATGTAAACT ACTTCTCTTG   1050

TTAGGTAATT TTTTTCACCT AGACTTTATT TCCCAATTGA GAAAAATATC   1100

TACTAAACAA AGCAGCAATA AAATATGATC ATCCTATCTG AGGAAAATAT   1150

CTCTTTTTCT GCCAGTGGAT TTTTAAAAAA TTGTAGTCAA CAAAAT       1196
```

\* \* \* \* \*

UNITED STATES PATENT AND TRADEMARK OFFICE
CERTIFICATE OF CORRECTION

PATENT NO.     : 6,448,381 B1
DATED          : September 10, 2002
INVENTOR(S)    : Deuel, Thomas, F. et al.

It is certified that error appears in the above-identified patent and that said Letters Patent is hereby corrected as shown below:

<u>Title page,</u>
Item [54], Title should be replaced with -- DNA ENCODING HEPARIN BINDING GROWTH FACTORS. --

<u>Column 1,</u>
Line 55, delete "." which appears after ";" and before "Zhan."

<u>Column 5,</u>
Line 9, nucleotide 314, should be changed from "d" to -- G. --
Line 62, "the extra space which appears after "ity" should be removed.

<u>Column 10,</u>
Line 6, add -- . -- between "7.0" and "About."
Table II, "HBGF8" should be replaced with -- 95% GLY-LYS-LYS-GLU-LYS-PRO-GLU-LYS-LYS-VAL-LYS-LYS-SER-ASP-CYS-GLY-GLU-TRP-GLN-TRP-SER-VAL-CYS-VAL-PRO. --
Line 57, add a space after "5299" and before "(1979)".

<u>Column 12,</u>
Line 50, the sequence of claim 2 should read:

```
GTCAAAGGCA  GGATCAGGTT  CCCCGCCTCC  CAGTCCAAAA  ATCCCGCCAA   50

GAGAGCCCCA  GAGCAGAGGA  AAATCCAAAG  TGGAGAGAGG  GGAAGAAAGA  100

GACCAGTGAG  TCATCCGTCC  AGAAGGCGGG  GAGAGCAGCA  GCGGCCCAAG  150

CAGGAGCTGC  AGCGAGCCGG  GTACCTGGAC  TCAGCGGTAG  CAACCTCGCC  200

CCTTGCAACA  AAGGCAGACT  GAGCGCCAGA  GAGGACGTTT  CCAACTCAAA  250

AATGCAGGCT  CAACAGTACC  AGCAGCAGCG  TCGAAAATTT  GCAGCTGCCT  300

TCTTGGCATT  CATTTTCATA  CTGGCAGCTG  TGGATACTGC  TGAAGCAGGG  350

AAGAAAGAGA  AACCAGAAAA  AAAAGTGAAG  AAGTCTGACT  GTGGAGAATG  400

GCAGTGGAGT  GTGTGTGTGC  CCACCAGTGG  AGACTGTGGG  CTGGGCACAC  450

GGGAGGGCAC  TCGGACTGGA  GCTGAGTCCA  AGCAAACCAT  GAAGACCCAG  500
```

UNITED STATES PATENT AND TRADEMARK OFFICE
CERTIFICATE OF CORRECTION

PATENT NO.   : 6,448,381 B1
DATED        : September 10, 2002
INVENTOR(S)  : Deuel, Thomas, F. et al.

It is certified that error appears in the above-identified patent and that said Letters Patent is hereby corrected as shown below:

Column 12 (cont'd),

| | | | | | |
|---|---|---|---|---|---|
| AGATGTAAGA | TCCCCTGCAA | CTGGAAGAAG | CAATTTGGCG | CGGAGTGCAA | 550 |
| ATACCAGTTC | CAGGCCTGGG | GAGAATGTGA | CCTGAACACA | GCCCTGAAGA | 600 |
| CCAGAACTGG | AAGTCTGAAG | CGAGCCCTGC | ACAATGCCGA | ATGCCAGAAG | 650 |
| ACTGTCACCA | CTCCCAAGCC | CTGTGGCAAA | CTGACCAAGC | CCAAACCTCA | 700 |
| AGCAGAATCT | AAGAAGAAGA | AAAAGGAAGG | CAAGAAACAG | GAGAAGATGC | 750 |
| TGGATTAAAA | GATGTCACCT | GTGGAACATA | AAAAGGACAT | CAGCAAACAG | 800 |
| GATCAGTTAA | CTATTGCATT | TATATGTACC | GTAGGCTTTG | TATTCAAAAA | 850 |
| TTATCTATAG | CTAAGTACAC | AATAAGCAAA | AACAAAAGA  | AAAAAAAAAA | 900 |
| AAAAAAAAAA | AAAAAAAAAA | AAAAAAAAAA | AAAAAAAAAA | AAAAAAAAAA | 950 |
| AAAAAAAAAA | A          |            |            |            | 961 |

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,448,381 B1
DATED         : September 10, 2002
INVENTOR(S)   : Thomas F. Deuel et al.

It is certified that error appears in the above-identified patent and that said Letters Patent is hereby corrected as shown below:

Column 12,
Line 48, add -- purified and isolated -- after "The".

Signed and Sealed this

Twenty-fifth Day of October, 2005

JON W. DUDAS
*Director of the United States Patent and Trademark Office*